United States Patent [19]

Loeb

[11] 4,078,625

[45] Mar. 14, 1978

[54] MOISTURE INDICATOR FOR HANGING PLANT CONTAINERS

[76] Inventor: Robert D. Loeb, 678 Deer Park Ave., Babylon, N.Y. 11702

[21] Appl. No.: 767,201

[22] Filed: Feb. 9, 1977

[51] Int. Cl.² ............................................. G01G 3/02
[52] U.S. Cl. .................................................. 177/233
[58] Field of Search ............................... 177/233, 225

[56] References Cited

U.S. PATENT DOCUMENTS

| 264,070 | 9/1882 | Forschner | 177/233 |
|---|---|---|---|
| 1,141,562 | 6/1915 | Law | 177/233 X |
| 3,967,578 | 7/1976 | Gallo | 177/225 X |

*Primary Examiner*—George H. Miller, Jr.
*Attorney, Agent, or Firm*—Robert D. Farkas

[57] ABSTRACT

An apparatus having a spring biased shaft provides vertical support to a hanging plant container. The weight of the container reflects the moisture content of the soil stored within the container. A plurality of bars are secured to the shaft providing a sight utilized in conjunction with a scale calibrated in terms of the moisture content of the soil, thereby advising the user when the plant needs water, or when a dangerous drought condition exists. An eye-hook is swivelably secured to the apparatus permitting the apparatus to be suspended downwardly from an overhead supporting surface, and permitting the plant to be rotated. A hook is formed at the lowermost end of the shaft, facilitating convenient support for the hanging plant container. Means are provided to adjustably vary the compression of the spring thereby allowing various size plant containers and plants to be utilized by the apparatus. An adjustable band encircles the apparatus and is positioned at a selected location indicating the maximum weight of a thoroughly soaked plant container thereby advising the user as to the maximum amount of water to be added to the container before encountering plant root rot or overflow spillage of the water.

5 Claims, 3 Drawing Figures

MOISTURE INDICATOR FOR HANGING PLANT CONTAINERS

BACKGROUND OF THE INVENTION

1. Field of the Invention

This invention relates to spring scales and more particularly to that class adapted to weight containers carrying fluids.

2. Description of the Prior Art

The prior art abounds with spring scales apparatus useful in weighing a variety of objects. U.S. Pat. No. 479,718 issued on July 26, 1892 to F. H. Morgan, et al., teaches a pair of tubular bodies, one being slidably engaged within the other, being disposed at a preferred location relative one another by a spring, co-axially aligned with and contained within both tubular bodies. Extending the spring, such as by adding a weight to the inner tubular body, causes indicia carried by the inner tubular body, to become exposed. A port in the outer tubular body is provided with a sight line permitting the numerical indicia to indicate the weight of the object suspended by the innermost tubular body.

U.S. Pat. No. 3,107,745 issued on Oct. 22, 1963 to A. F. Dujan discloses a pair of triangularly shaped hollow elements disposed one within the other and secured together by a spring element extending between them. A vessel containing medicaments is suspended from below the innermost element having its weight measured by indicia carried by the innermost element, read through the transparent outermost element. A slide element, comprising a pair of pointers, is frictionally engaged with one apex of the outermost triangularly shaped element and is useful in determining the terminal desired weight of the liquid container suspended from the apparatus as well as intermediate weights.

Both of the aforementioned patents suffer the common deficiency of providing a single or at best a double sight line for measuring the weight of the suspended article, wherein the weight is expressed in units of volume or weight units. Furthermore, both apparatus fail to provide a vernier adjustment capable of compensating for the weight of a growing plant carried by a suspended container.

SUMMARY OF THE INVENTION

A primary object of the present invention is to provide an apparatus which expresses the condition of the amount of moisture of the soil in a hanging plant carrying container, with a high degree of accuracy.

Another object of the present invention is to provide an apparatus which once calibrated, indicates the minimum weight that the container, plant and drying soil should be before water is added.

Still another object of the present invention is to provide an apparatus which, once calibrated, indicates the maximum weight that the container, plant, soil and added water should be before overwatering occurs.

Another object of the present invention is to provide an apparatus which can be adjusted to offset a change in the weight of the plant as it grows, thus providing a measure of the soil moisture with a high degree of adaptability.

Yet another object of the present invention is to provide an apparatus which may be adjusted to handle a variety of different sized containers, plants and quantities of soil with equal accuracy.

A further object of the present invention is to provide an apparatus which may be rotated for even light exposure and still be viewed from four directions, wherein each direction is suitable to indicate the status of the moisture content of the soil at any given point in time.

Spring scales have been known for many years. However, a spring scale which may be adjustably calibrated to measure the weight of a suspended plant container and plant so as to express the status of the moisture content of the soil supporting the plant whilst providing a readout in terms of the moisture content of the soil and in terms of the minimum weight of the dry soil and in terms of the maximum weight of fully soaked soil, is novel and highly desirable to amateur horticulturists as well as professional plant growers. The process of growing a plant within a container, such as a flower pot, requires carefully controlled watering at a rate determined by the moisture content of the air, the size and health of the plant, the size of the container, the type of plant, and the amount of soil disposed within the container and supporting the plant. In the extremes, overwatering can cause root rot and underwatering can cause plant death. An inexperienced plant grower finds it difficult to judge the moisture content within the soil, often times vacillating between adding too much water or not adding water when the plant requires same.

The present invention, once calibrated, permits the amateur to tell at a glance whether water is required and to suggest the maximum amount of water that is needed by the plant. This is accomplished by starting with a dry (just ready to water) plant and then adjusting the spring tension so that indicator bars are in the "dry" position. The plant soil is watered to a maximum amount and a ring about the device is then adjusted to a point where the indicator bars of the device are disposed measuring the weight of the container and the soil therewithin so as to be just above to the ring. Furthermore, small variations in the size of the plant may be accommodated by adjustably varying the compression of the spring element of the scale. The indicia indicating the moisture of the soil is expressed in terms of dryness and wetness as opposed to a weight measure, thereby permitting the user to quickly discern the need to water the plant.

These objects as well as other objects of the present invention will become more readily apparent after reading the following description of the accompanying drawings.

DESCRIPTION OF THE PREFERRED EMBODIMENT

Figures 1, 2:
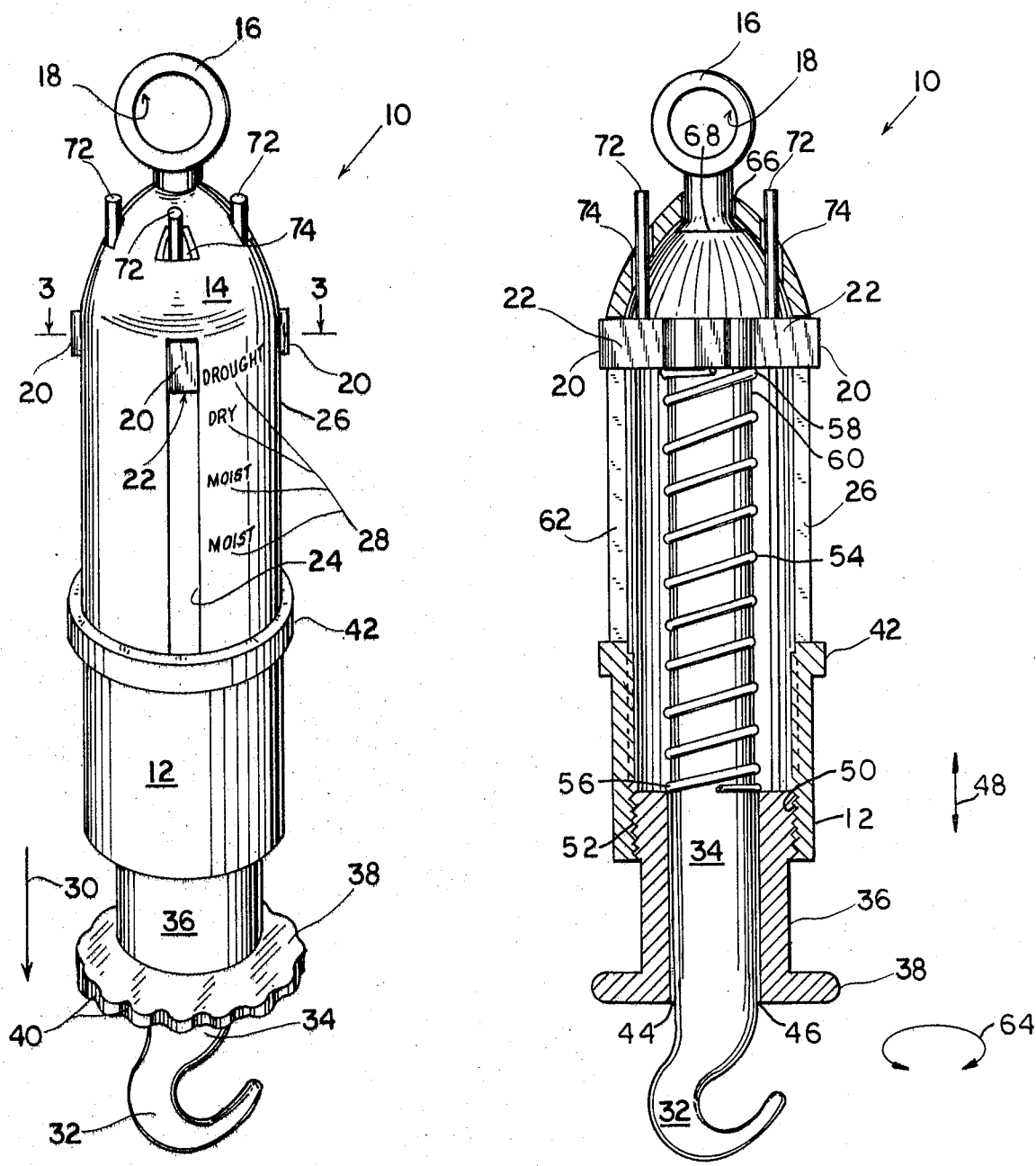
FIG. 1 is a perspective view of the present invention.
FIG. 2 is a front elevation cross-sectional view of the present invention.

The structure and method of fabrication of the present invention is applicable to a hollow bullet shaped tubular element carrying an eye hook attachment swivelably engaged within an opening disposed at the pointed end thereof. The inner cylindrical surface, disposed adjacent the open mouth portion of the bullet shaped element carries a number of female threads adjacent the open mouth portion thereof. A rod having a cylindrical exterior surface, adapted with male threads at one end thereof, threadingly engages the female threads such that the rod may enter within the bullet shaped element and may be positioned at selected locations so as to have a portion of this rod positioned variably between the open mouth portion and the pointed end of the bullet shaped element. A shaft is disposed within the hollow portion of the bullet shaped element, having a portion of its length passing through an opening or passageway within the rod and having one free end thereof emerging outwardly from the rod and fashioned into a hook. The other end of the rod carries four bars, each disposed at right angles to each other and each extending radially outwardly from the longitudinal axis of the shaft, and four additional upwardly directed bars, extending upwardly through four openings at the uppermost end of the bullet shaped element. The free ends of the additional upwardly directed bars are colored so as to indicate a drought or very dry condition of the soil. The free end of each upwardly directed bar passes thorugh a slot. Thus, four slots are utilized, each being disposed parallel to each other at locations ninety degrees apart about the periphery of the bullet shaped tubular element. Indicia is disposed adjacent the slots, expressed in terms of words and colors such as drought (red), dry, moist, wet (green), and the like. A ring is slidably affixed about the exterior tubular surface of the bullet shaped element, utilizing friction forces there-in-between such that the ring may be disposed manually at selected locations along the length of the tubular element. The user, once having carefully allowed the plant container and the soil thereby to become dry, that is, to the state of needing water, adjusts the lower tubular element so that the indicator bars are adjacent to the "dry" position. The user then thoroughly waters the pot to the point of near overflowing, when suspended by the hook and when the entire apparatus is suspended depending downwardly from an overhead supporting structure from the swivelable eye hook, simply adjusts the ring to a position below the displaced location of the free ends of the bars. This position of the ring indicates the weight of the plant container, plant and soil when thoroughly moistened thereby serving as a guide for the maximum amount of water to be added during subsequent watering operations.

A flange-like ring, extending radially outwardly from the rod, and adapted with undulations in the outermost edges thereof, permits the rod to variably compress the spring so as to calibrate the apparatus for different size plant containers, weights of soil, size of plants, and for plant growth as it occurs.

Now referring to the Figures, and more particularly to the embodiment illustrated in FIG. 1 showing the present invention 10 comprising an outermost hollow tubular body 12 having a bullet nosed pointed end 14. Eye hook 16 extends outwardly from the pointed end 14 containing an opening 18 utilized to support the present invention depending downwardly from an uppermost supporting hook, not shown. The free ends 20 of bars 22 extend through slots 24 and 26. Indicia 28 comprising the words dry and moist is carried by the external cylindrical surface of body 12. Bars 22 are free to move downwardly from the positions shown in the directions of arrow 30 when a plant container, not shown, containing soil and a plant is suspended from hook-like end 32 of shaft 34. Cylinder 36 is engaged partially within the interior of body 12 and has a portion extending outwardly therefrom. Flange 38 is fixedly secured to rod 36 and is adapted with a plurality of finger gripping undulations 40 on the marginal edge thereof. Ring 42 frictionally engages the exterior cylindrical surface of body 12 such that the ring may be positioned along the length of body 12 at any preferred location therealong. Bars 72, pass through openings 74 located near the nose or swivel end of the bullet shaped housing and rise up when the soil becomes very dry. The free ends of the bars may be brightly colored serving as an easily seen warning signal of dangerous drought conditions.

FIG. 2 illustrates the open mouth portion 44 of body 12 through which is disposed a portion of the length of cylinder 36. Shaft 34 passes through passageway 46 located in cylinder 36 such that shaft 34 may freely slide in the directions of arrows 48. Cylinder 46 is provided with male threads 50 threadingly engaged with female threads 52 disposed on the interior cylindrical surface of body 12. Helical spring 54 is shown carried by shaft 34, having end 56 supported by cylinder 36 and end 58 in touching engagement with bar 22. Bar 22 is fixedly secured to end 60 of shaft 34 and extends passing through slot 26 and slot 62 in body 12. Ring 42 may be adjustably located along the length of body 12 in the directions of arrows 48. Rod 36 may be positioned at a preferred vertical location when flange 38 is manually located in the directions of arrows 64, thereby variably compressing spring 54. Eye hook 16 passes through opening 66 and is adapted with a flaired-out portion 68 permitting eye hook 16 to swivel within opening 66. Opening 66 is substantially smaller than open mouth portion 44.

Figure 3:
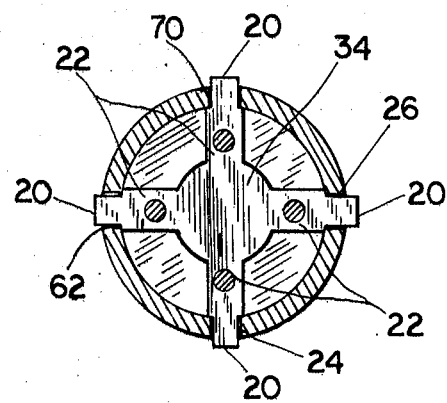
FIG. 3 is a plan view taken along line 3—3 viewed in the direction of arrows 3—3 as shown in FIG. 1.

FIG. 3 shows slots 24, 26, 62 and 70 through which bars 22 pass. Free ends 20 of bars 22 are visible at locations disposed apart 90° along the surface of body 12.

One of the advantages of the present invention is an apparatus which expresses the condition of the amount of moisture of the soil in a hanging plant carrying container, with a high degree of accuracy.

Another advantage is an apparatus which once calibrated, indicates the minimum weight that the container, plant and drying soil should be before water is added.

Still another advantage is an apparatus which, once calibrated, indicates the maximum weight that the container, plant, soil and added water should be before overwatering occurs.

Another advantage is an apparatus which can be adjusted to offset a change in the weight of the plant as it grows, thus providing a measure of the soil moisture with a high degree of adaptability.

Yet another advantage is an apparatus which may be adjusted to handle a variety of different sized containers, plants and quantities of soil with equal accuracy.

A further advantage is an apparatus which may be rotated for even light exposure and still be viewed from four directions, wherein each direction is suitable to indicate the status of the moisture content of the soil at any given point in time.

Thus, there is disclosed in the above description and in the drawings, an embodiment of the invention which fully and effectively accomplishes the objects thereof. However, it will become apparent to those skilled in the art, how to make variations and modifications to the instant invention. Therefore, this invention is to be limited, not by the specific disclosure herein, but only by the appending claims.

The embodiment of the invention in which an exclusive privilege or property is claimed are defined as follows:

I claim:

1. An indicator support for hanging plant containers comprising an elongated hollow tubular body having one end thereof carrying a plurality of internal threads disposed adjacent an open mouth portion thereof, the other end of the body being disposed having an opening, an eye hook being disposed swivelably passing through the opening and providing vertical support to the body, a rod having a passageway extending along the longitudinal axis thereof, the rod carrying complementary external threads being disposed threadingly engaged with the plurality of internal threads, a shaft, a portion of the length of the shaft being disposed slidably engaged within the passageway, one end of the shaft being disposed forming a hook, the other end of the shaft being disposed within the tubular body, said one end of the shaft being disposed outwardly of the passageway and the body, a plurality of slots piercing the walls of said body, each of the slots being disposed in parallel relationship to the other slots and extending parallel to the longitudinal axis of the body, a plurality of bars fixedly secured to the other end of the shaft and extending radially outwardly therefrom, the free ends of the bars passing through the plurality of slots being disposed in slidable relationship therealong, a helical spring, the helical spring carried by the shaft, one end of the spring being disposed in touching engagement with the rod, the other end of the spring being disposed in touching engagement with the bars, indicia being disposed on the exterior surface of the body adjacent to at least one of the slots, said indicia indicating the moisture content of a plant container depending downwardly from the hook.

2. The indicator support for hanging plant containers as claimed in claim 1 further comprising a ring slidably frictionally engaged along the exterior surface of the body and being disposed at selected locations therealong.

3. The indicator support for hanging plant containers as claimed in claim 1 further comprising a flange fixedly secured to said rod, the flange extending radially outwardly from the rod and being disposed intermediate the open mouth portion of the body and the hook.

4. The indicator support for hanging plant containers as claimed in claim 1 wherein said opening is circular in shape having a smaller diameter than said open mouth portion of the body.

5. The indicator support for hanging plant containers as claimed in claim 1 further comprising a plurality of upwardly directed bars, one end of each of said upwardly directed bars fixedly secured to said other end of said shaft, said body having a plurality of holes therein, said holes located adjacent said opening, a portion of each of said upwardly directed bars passing through said holes, the longitudinal axis of each of said upwardly directed bars extending parallel to the longitudinal axis of said body.

* * * * *